(12) United States Patent
Schlienger et al.

(10) Patent No.: US 8,257,409 B2
(45) Date of Patent: Sep. 4, 2012

(54) REFERENCE PIN

(75) Inventors: Andrè Schlienger, Münchenstein (CH); Markus Buettler, Oensingen (CH); Peter Senn, Waldenburg (CH)

(73) Assignee: Synthes USA, LLC, West Chester, PA (US)

(*) Notice: Subject to any disclaimer, the term of this patent is extended or adjusted under 35 U.S.C. 154(b) by 1119 days.

(21) Appl. No.: 11/910,481

(22) PCT Filed: Apr. 5, 2006

(86) PCT No.: PCT/CH2006/000195
§ 371 (c)(1),
(2), (4) Date: May 6, 2008

(87) PCT Pub. No.: WO2006/105685
PCT Pub. Date: Oct. 12, 2006

(65) Prior Publication Data
US 2008/0312702 A1 Dec. 18, 2008

(30) Foreign Application Priority Data

Apr. 6, 2005 (CH) .............................. 2005/000195

(51) Int. Cl.
*A61B 17/04* (2006.01)
(52) U.S. Cl. ......................................... 606/329; 606/96
(58) Field of Classification Search .............. 606/62–68, 606/96–98, 300–331, 87–89, 104
See application file for complete search history.

(56) References Cited

U.S. PATENT DOCUMENTS

| | | | | |
|---|---|---|---|---|
| 4,541,424 A * | 9/1985 | Grosse et al. | | 606/98 |
| 4,621,628 A * | 11/1986 | Brudermann | | 606/97 |
| 5,234,434 A * | 8/1993 | Goble et al. | | 606/96 |
| 5,411,503 A * | 5/1995 | Hollstien et al. | | 606/86 R |
| 5,478,343 A * | 12/1995 | Ritter | | 606/97 |
| 5,665,086 A * | 9/1997 | Itoman et al. | | 606/64 |
| 5,766,179 A * | 6/1998 | Faccioli et al. | | 606/98 |
| 6,039,742 A * | 3/2000 | Krettek et al. | | 606/96 |
| 6,379,364 B1 * | 4/2002 | Brace et al. | | 606/96 |
| 6,656,189 B1 * | 12/2003 | Wilson et al. | | 606/97 |
| 7,549,994 B2 * | 6/2009 | Zander et al. | | 606/99 |
| 7,588,577 B2 * | 9/2009 | Fencl et al. | | 606/96 |
| 7,887,545 B2 * | 2/2011 | Fernandez et al. | | 606/97 |
| 7,942,875 B2 * | 5/2011 | Nelson et al. | | 606/63 |
| 2003/0018335 A1 | 1/2003 | Michelson | | |

FOREIGN PATENT DOCUMENTS

WO 02/19931 3/2002

* cited by examiner

*Primary Examiner* — Thomas C. Barrett
*Assistant Examiner* — Christopher Beccia
(74) *Attorney, Agent, or Firm* — Fay Kaplun & Marcin, LLP

(57) ABSTRACT

Described is a reference pin for use during a bone fracture treatment. The pin may include a longitudinal shaft and a spreading member. The longitudinal shaft with a longitudinal axis, a front end, a rear end and a through hole penetrating the shaft from the front end to the rear end. The shaft includes a rear portion adjoining the rear end and an expandable front portion adjoining the front end. The expandable front portion is insertable in a distal locking hole of an intramedullary nail and reversibly expandable transversely to the longitudinal axis. The spreading member is moveably located in the through hole and apt for reversibly expanding the expandable front end portion. The expandable front portion is reversibly expandable within a range between 0.3 mm and 0.5 mm.

19 Claims, 5 Drawing Sheets

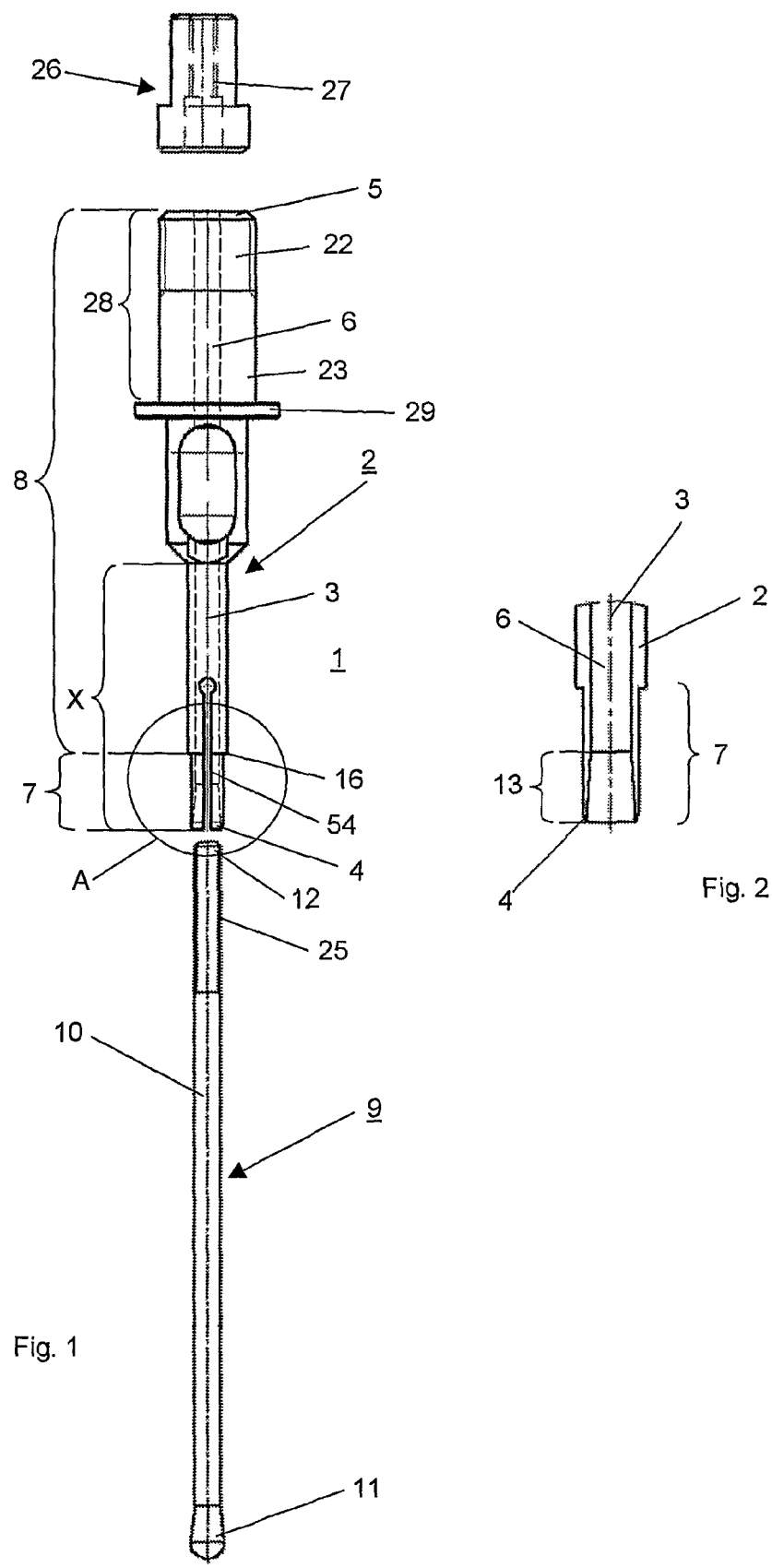

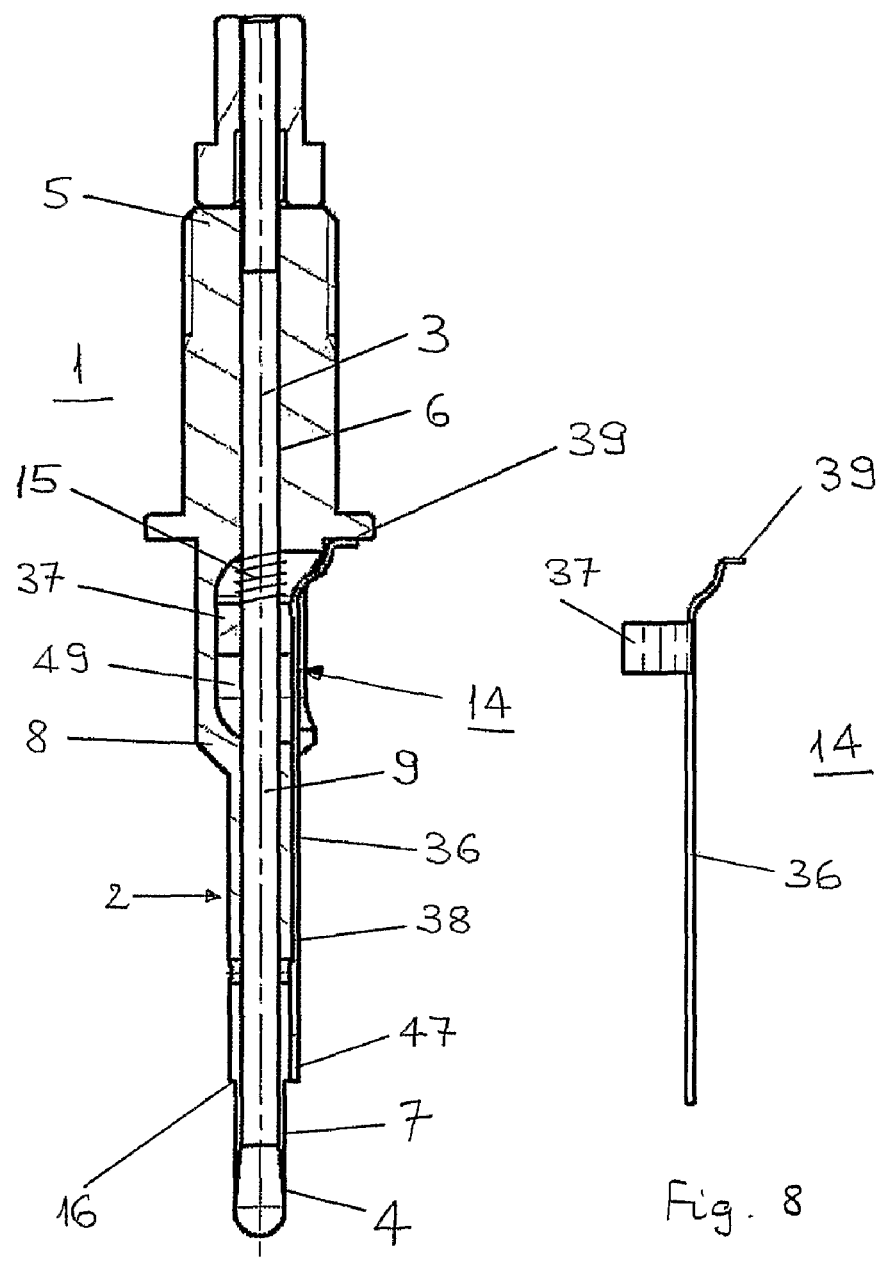

REFERENCE PIN

FIELD OF THE INVENTION

The invention relates to a reference pin for aligning a drill guide to an intramedullary nail.

Intramedullary nails that are used e.g. for the treatment of long bone fractures are usually provided with interlocking holes transversely penetrating the intramedullary nail. One or more of these locking holes are situated at the proximal end as well as at the distal end of the intramedullary nail. These locking holes allow the passage of locking screws that will interlock with the bone and are suitable for the anchoring of the intramedullary nail to the bone. The locking screws are inserted medio-lateral into the bone and through the nail after insertion of the intramedullary nail in the intermedullary channel of the bone. Therefore, bores being coaxial to the locking holes of the nail must be drilled into the bone after insertion of the intramedullary nail in the intramedullary channel. Usually, aiming devices for guiding the drill are used. Said aiming devices are connectable at one end of the intramedullary nail. The locking of the far end of the intramedullary nail is effected optically using an X-ray apparatus and a radiolucent drill gear or without X-ray apparatus by means of a costly aiming device. The consequences are often high radioscopy duration and high radiation exposure for the patient or a complex time consuming apparatus.

DESCRIPTION OF THE PRIOR ART

WO 92/01422 CHADWICK discloses a drill guide device being provided with a reference element at the distal end which may be screwed in one of the distal locking holes of the intramedullary nail. Due to this reference element the drill guide device is fixedly aligned with the intramedullary nails and the distal locking holes may be drilled without optical control using an X-ray apparatus. Only the reference element has to be inserted into the respective locking hole at the distal end of the interlocking intramedullary nail with use of radiography so that during insertion of the locking screws no radiography is required and less time is needed for fixation of the intramedullary nail in the bone. Furthermore, missdrilling may be avoided. However, this known drill guide device shows the disadvantage that
a) the reference element must be inserted into an additional transverse location hole of the intramedullary nail which must be provided with an interior thread may not be used for insertion of a locking screw and which further weakens the distal end of the intramedullary nail;
b) this known reference element is not suitable for small sized and/or cannulated intramedullary nails due to the necessity of the interior thread of a certain length in the location hole; and
c) the insertion of the screw of the reference element into the distal locking hole requires a time consuming alignment due to the matching diameters of the threads at the screw and in the distal locking hole of the intramedullary nail.

SUMMARY OF THE INVENTION

It is therefore an object of the invention to provide a reference element being insertable and reversibly fastenable in a distal locking hole of an intramedullary nail which must not be provided with an interior thread and which has an expandable front portion of the reference pin having a suitable clearance in the distal locking hole of the intramedullary nail such allowing an easy insertion of the pin into the locking hole.

The above object is solved by means of a reference pin 1 for use during bone fracture treatment comprising a longitudinal shaft with a front end, a rear end and a through hole penetrating said shaft from said front end to said rear end, whereby said shaft further comprises a rear portion adjoining said rear end and an expandable front portion adjoining said front end; said expandable front portion being insertable in a distal locking hole of an intramedullary nail and being reversibly expandable transversely to the longitudinal axis of said shaft. Furthermore, said reference pin includes a spreading member moveably located in said through hole and being apt for reversibly expanding said expandable front end portion.

The following advantages may be achieved by means of the reference pin according to the invention:
the expandable front portion of the reference pin may have a suitable clearance with respect to the distal locking hole of the intramedullary nail thus allowing an easy insertion of the reference pin into the distal locking hole and a subsequent exact alignment of the reference pin relative to the locking hole due to the expansion of the expandable portion of the reference pin;
insertion and fastening of the reference pin in an intramedullary nail without interior thread in the distal locking holes thus avoiding a further reduction of the mechanical strength through stress concentration caused by the threads in the area of the distal locking holes which is already loaded at most; and
insertion and fastening of the reference pin in intramedullary nail with small nail diameters and slotted intramedullary nails where a compression of the nail diameter must be avoided.

In a preferred embodiment said spreading member is a pin coaxially displaceable in said through hole, said pin comprising a wedge-shaped or conical leading end and a trailing end. A wedge or cone connection allows a simple expanding procedure of the front portion. Furthermore, such a wedge or cone connection permits a smooth fastening of the expandable portion within the locking hole of the intramedullary nail without a great expenditure of force. Preferably, the leading end of the pin is conically shaped with a length of 5 mm and a cone angle between 3° and 5°, typically 3.4°.

In another embodiment said through hole has a preferably continuously enlarging section adjoining said front end of said shaft, said preferably continuously enlarging section being shaped complementarily with said leading end of said pin. Instead of being continuously a discontinuously enlarging section may be provided in said through hole.

In a further embodiment the expandable front portion is reversibly expandable within a range between 0.3 mm and 0.5 mm, thus allowing the advantage of an easy insertion into the distal locking hole of the intramedullary nail when the expandable front portion is in its non-expanded state.

In another embodiment said expandable front portion is integral with said shaft, thus allowing the advantage that in case of a metallic shaft the expandable front portion may be configured resiliently by manufacturing axial slots into the cannulated front portion of the shaft such allowing an uncomplicated fabrication of the shaft.

In still another embodiment said wedge-shaped or conical leading end enlarges towards said leading end of said pin. Herewith, the advantage is achieved that in case of a wedge or cone lock getting jammed the wedge or cone lock may be released by exerting axial impacts on the trailing end of the pin.

In a further embodiment said expandable front portion is nonpositively fastenable in a distal locking hole of an intramedullary nail by means of frictional forces.

In still a further embodiment the shaft comprises a shoulder at the transition between the rear portion and the expandable front portion, said shoulder being directed towards the front end of said shaft for abutting the outer surface of an intramedullary nail. Thus, a defined abutment of the reference pin at the outer surface of the intramedullary nail is achieved by means of said shoulder with respect to the longitudinal axis of said reference pin.

In another embodiment said reference pin comprises securing means permitting a defined positioning of the reference pin within a corresponding hole with regard to rotation about the longitudinal axis of said reference pin.

In yet another embodiment said shaft additionally comprises a depth indicator. The depth indicator allows a visual control of the insertion of the reference pin until the shoulder abuts the outer surface of the intramedullary nail and thus the reference pin being completely inserted in the locking hole of the intramedullary nail.

In a further embodiment the depth indicator is arranged coaxially slideable at the lateral surface of said shaft.

In still a further embodiment said depth indicator is resiliently biased towards the front end of said shaft by means of a resilient member.

In another embodiment said spreading member comprises a nut member with an interior thread and said pin has an exterior thread terminally arranged towards its trailing end. This embodiment allows the advantage that the pin is axially displaceable by means of the nut member so that the expanding procedure of the expandable front portion of the reference pin may be easily effected by tightening the nut member.

In still another embodiment said reference pin comprises a reference element with markers the position of which is acoustically or electromagnetically detectable by means of a position measurement device of a surgical navigation system.

In a further embodiment said reference pin is made of a radiolucent material and includes at least two radiopaque markers, thus allowing the advantage of a full X-ray control.

In still a further embodiment the shaft comprises a threaded terminal rear portion and a stop axially spaced towards the front end of said shaft.

In another embodiment the shaft comprises at least one axial slot extending on at least the expandable front portion of said shaft.

In still another embodiment said reference pin is made of a metallic material, preferably of hardened steel.

In a further embodiment the shaft is made of a material being softer than the material of the spreading member.

Furthermore, an assembly for locking an intramedullary nail according to the invention is provided comprising a reference pin and further comprising a U-shaped drill guide having at least two guide holes having bore axes which extend transversely to the longitudinal axis of said reference pin and wherein said U-shaped defines a plane which is not cut neither by the longitudinal axis of said reference pin nor by the bore axes.

Additionally, an assembly for bone fragment fixation according to the invention is provided comprising a reference pin and a U-shaped device for fractured bone fixation having a bow shaped member forming an arc in a plane which is not cut by the longitudinal axis of said reference pin, said device further having slots extending along an arc on the periphery of said bow shaped member, whereby said device further comprises drill sleeves which are slideable in the slots and reversibly fastenable once located at a desired position.

A BRIEF DESCRIPTION OF THE DRAWINGS

Several embodiments of the invention will be described in the following by way of example and with reference to the accompanying drawings in which:

FIG. 1 shows an explosive view of an embodiment of the reference pin according to the invention;

FIG. 2 shows a magnified longitudinal section according to circle A in FIG. 1

FIG. 7 shows a longitudinal cross section through a further embodiment of the reference pin according to the invention;

FIG. 8 shows a lateral view of a depth indicator used in the embodiment shown in FIG. 7.

DETAILED DESCRIPTION

Figure 3:
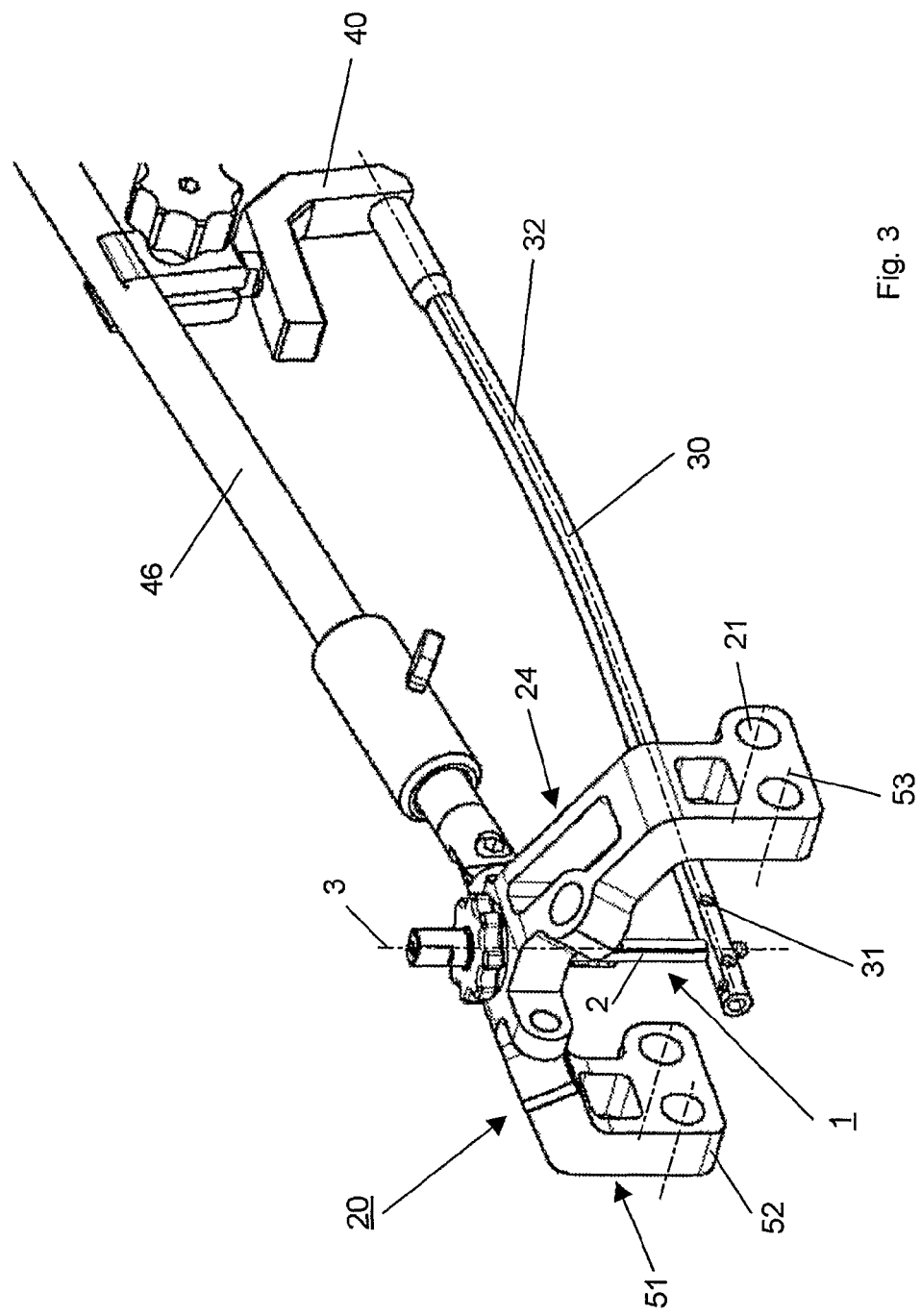
FIG. 3 shows a perspective view of an assembly comprising an embodiment of the reference pin according to the invention being attached to an intramedullary nail and having a drill guide mounted.

FIGS. 1 and 2 depict an embodiment of the reference pin 1, said reference pin 1 comprising a longitudinal shaft 2 with a longitudinal axis 3, a front end 4, a rear end 5 and a through hole 6 penetrating said shaft 2 from said front end 4 to said rear end 5. Furthermore, said shaft 2 a rear portion 8 adjoining said rear end 5 and an expandable front portion 7 adjoining said front end 4, whereby said expandable front portion 7 is insertable in a distal locking hole 31 of an intramedullary nail 30 (FIG. 3) and is reversibly expandable transversely to said longitudinal axis 3. Additionally, a spreading member 9 is provided which is configured as a pin 10 coaxially displaceably located in said through hole 6 and being apt for reversibly expanding said expandable front end portion 7 by means of a cone connection formed by a conical leading end 11 of the pin 10 and a corresponding conically enlarging section 13 in the through hole 6 in the reference pin 1. Said through hole 6 has a continuously enlarging section 13 adjoining said front end 4 of said shaft 2 which is shaped complementarily to said conical leading end 11 of said pin 10, whereby said enlarging section 13 as well as said conical leading end 11 enlarge towards said front end 4 of said shaft 2, respectively towards said leading end 11 of said pin 10.

The reference pin 1 further comprises a nut member 26 abutting the rear end 5 of the shaft 2 and having an interior thread 27 matching a corresponding exterior thread 25 at a terminal rear portion of said pin 10 therewith allowing a coaxial displacement of the pin 10, whereby upon tightening the nut member 26 the expandable front portion 7 of said shaft 2 is expanded transversely to the longitudinal axis 3 of said shaft 2 by means of the cone connection between the conical leading end 11 of the pin 10 and the conically enlarging section 13 of the through hole 6. The shaft 2 comprises two diametrically opposed axial slots 54 extending beyond the expandable front portion 7 of said shaft 2.

In order to attach the drill guide 20 (FIG. 3) to the rear end 5 of the shaft 2 said shaft 2 comprises a terminal rear portion 28 comprising an external thread 22 adjoining the rear end 5 of said shaft 2, directed towards the front end 4 of said shaft 2 subsequently arranged an unthreaded cylindrical portion 23 apt for matching a fixation hole (not shown) in the transverse portion 24 of said drill guide 20 and a stop 29 being formed by a radially enlarged section of said shaft 2. In order to fasten the reference pin 1 to the drill guide 20 the terminal rear portion 28 of said shaft is lead through said fixation hole in the transverse portion 24 of said drill guide 20 until the stop 29 abuts the surface of the transverse portion 24. Then a nut 50 is screwed onto the external thread 22 and tightened.

FIG. 3 shows the reference pin 1 being inserted in one of the distal locking holes 31 of an intramedullary nail 30. Furthermore, an essentially U-shaped drill guide 20 is mounted on the reference pin 1, whereby said drill guide 20 forms a bow parallel to a plane orthogonal to the nail longitudinal axis 32 and being essentially symmetrical to the longitudinal axis 3 of the reference pin 1. Said drill guide 20 comprises a transverse portion 24 including a central section being arranged orthogonally to the longitudinal axis 3 of said shaft 2 and angularly adjoining said central section two outer sections being connected to an arm 51 each at their far ends. Said arms 51 extend orthogonal to the central section of said transverse portion 24, i.e. parallel to the longitudinal axis 3 of said shaft 2.

Furthermore, said drill guide 20 is provided with guide holes 21 for drilling the holes of the locking screws, said guide holes 21 penetrating the parallel arms 51 near their free ends 52. The axes 53 of said guide holes 21 are perpendicular to the longitudinal axis 3 of said shaft 2 and to the longitudinal nail axis 32 in the distal region. The drill guide 20 is connected with the nail insertion handle 40 by means of a stabilisation and alignment rod 46 which is articulatedly attached with one of its ends at the drill guide 20 and with its other end at the nail insertion handle 40.

Figure 4:
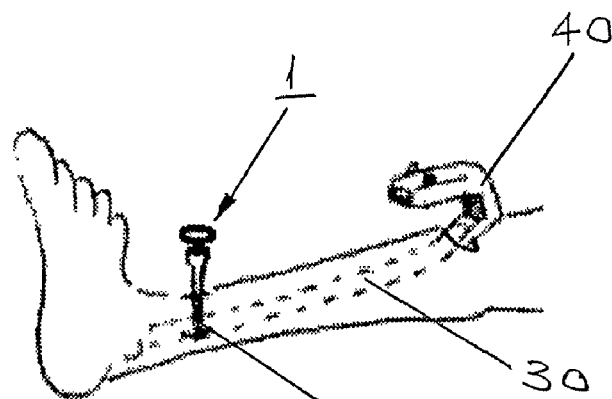
FIG. 4 shows a tibial portion of a patient's leg having an intramedullary nail inserted and an embodiment of the reference pin according to the invention fastened at the nail.
Figure 5:
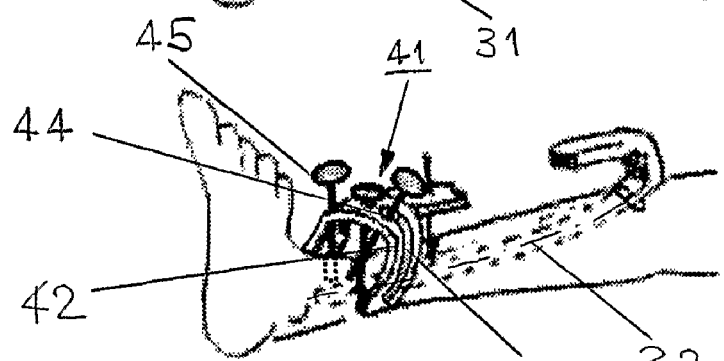
FIG. 5 shows a tibial portion of a patient's leg having an intramedullary nail inserted and an embodiment of the reference pin according to the invention fastened at the nail and a bone fixation device attached at the reference pin.
Figure 6:
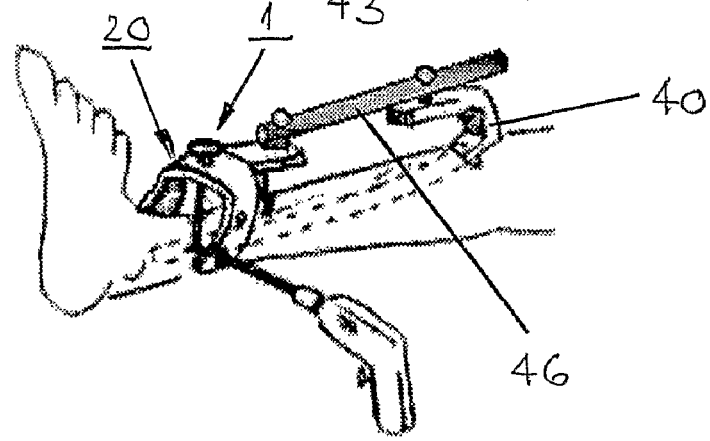
FIG. 6 shows a tibial portion of a patient's leg having an intramedullary nail inserted and an embodiment of the reference pin according to the invention fastened at the nail and a drill guide attached at the reference pin.

Brief Description of the Surgical Method:
1. Insertion of the interlocking intramedullary nail 30 into the bone using an insertion handle 40 attached to the proximal end of the intramedullary nail 30 according to the state of the art;
2. Drilling of a hole into the bone through one of the locking holes 31 at the distal end of the intramedullary nail 30 using a mobile X-ray apparatus;
3. Enlarge the near cortex with another drill to allow passage for the reference pin part X (FIG. 1);
4. Insertion of the expandable front portion 7 of the reference pin 1 (FIG. 1) into one of the locking holes 31 at the distal end of the intramedullary nail 30 using a mobile X-ray apparatus (FIG. 4);
5. Mounting and fixing of a device for fractured bone fragment fixation 41 (FIG. 5) which is provided with a bow shaped member 42 forming an arc in a plane orthogonal to the longitudinal nail axis 32 and a having slots 43 extending along an arc on the periphery of said bow shaped member 42. The device for fractured bone fragment fixation 41 further comprising drill sleeves 44 which are slideable in the slots 43 and reversibly fastenable once located at a desired position. The arc of the bow shaped member 42 is configured in such manner that the drill sleeves 44 are slideable on an arc having a possibility to be adjusted and locked with regard to their position for drilling and fixing the fractured bone fragments by means of an expandable portion;
6. Fixing of the bone fragments by means of pins 45 or bone screws lead through the central bores of the drill sleeves 44;
7. Removing the device for fractured bone fragment fixation 41;
8. Adjusting the drill guide 20 relative to the reference pin 1 and fastening the drill guide 20 at the reference pin 1 as well as at the nail insertion handle 40 by means of a stabilisation and alignment rod 46 and with respect to the nail longitudinal axis 32 (FIG. 6);
9. predrilling of the bone (FIG. 6) for the other distal locking holes 31 of the interlocking intramedullary nail 30 and inserting of the screws into the locking holes (with use or non-use of the drill guide 20);
10. Interlocking of the interlocking intramedullary nail 30 in the distal region by means of locking screws;
11. Removing of the drill guide 20 and reference pin 1;
12. Inserting a locking screw into this last distal locking hole; and
13. Locking the interlocking intramedullary nail 1 in the proximal portion by means of a aiming means attached to the insertion handle 40.

In FIG. 7 an embodiment of the reference pin 1 is depicted which differs from the embodiment shown in FIGS. 1 and 2 only therein that a depth indicator 14 (FIG. 8) is provided by means of which the surgeon may visually check when the shoulder 16 at the transition between the expandable front portion 7 and the rear portion 8 of said shaft 2 abuts the outer surface of the intramedullary nail 30 next to the locking hole 31 used for the reference pin 1. Said depth indicator 14 is located axially displaceable at the lateral surface 38 of said shaft 2 and includes a tracer pin 36 extending parallel to the longitudinal axis of said shaft 2 and a clamp 37 fixed to said tracer pin 36 in a rear section directed towards the rear end 5 of said shaft 2 by means of which said depth indicator 14 is attachable to said spreading member 9 in such manner that said tracer pin 36 may be displaced parallel to the longitudinal axis 3 of said shaft 2. The clamp 37 is retained in an hollow space 49 having an enlarged diameter with regard to the through hole 6. Said tracer pin 36 has a tip 47 directed towards the front end 4 of said shaft 2 and axially oppositely a pointer 39 being 90° offset to form an indicating arrow orthogonal to said longitudinal axis 3 of said shaft 2. Furthermore, a resilient member 15 in the form of a helical compression spring is arranged between the clamp 37 and a stop formed by the transition between the hollow space 49 and the through hole 6, said resilient member 15 such being apt to resiliently press said depth indicator 14 towards its foremost position.

Figure 9:
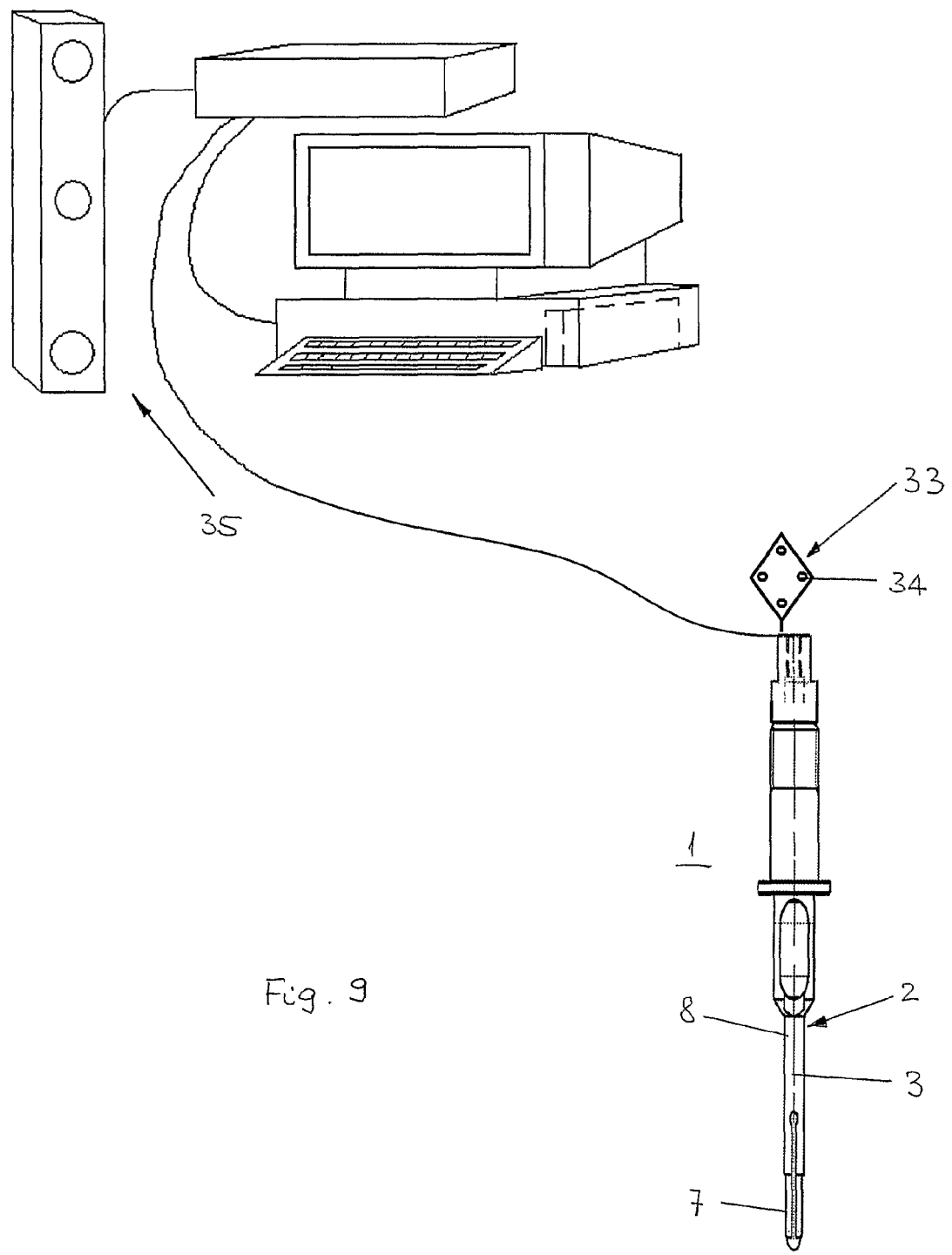
FIG. 9 shows a lateral view of yet a further embodiment of the reference pin according to the invention together with a computer assisted surgical navigation system.

FIG. 9 depicts an embodiment of said reference pin 1 being apt as a reference means for spatially referencing e.g. a surgical implant, a surgical instrument or a bone using a computer assisted surgical navigation system. Said reference pin 1 only differing from the embodiment shown in FIGS. 1 and 2 by the fact that it additionally comprises a reference element 33 with markers 34 the position of which is acoustically or electromagnetically detectable by means of a position measurement device 35 of a surgical navigation system and a rotational securing means (not shown), e.g. a flattened or polygonal section at the transition between the expandable front portion 7 and the rear portion 8 of the shaft 2 such allowing a defined positioning of the reference pin 1 with respect to another surgical device and avoiding a rotation of said reference pin 1 about the longitudinal axis 3 of the shaft 2.

What is claimed is:
1. A reference pin for use during a bone fracture treatment, comprising:
a longitudinal shaft with a longitudinal axis, a front end, a rear end and a through hole penetrating the shaft from the front end to the rear end, the shaft including a rear portion adjoining the rear end and an expandable front portion adjoining the front end, the expandable front portion being insertable in a distal locking hole of an intramedullary nail and being reversibly expandable transversely to the longitudinal axis, the through hole having a continuously enlarging section adjoining the front end of the shaft, wherein the continuously enlarging section enlarges towards the front end; and a spreading member moveably located in the through hole and being apt for reversibly expanding the expandable front end portion, wherein the expandable front portion is reversibly expandable within a range between 0.3 mm and 0.5 mm.

2. The reference pin of claim 1, wherein the spreading member is a pin coaxially displaceable in the through hole, the pin comprising a trailing end and one of (a) a wedge-shaped and (b) conical leading end.

3. The reference pin of claim 2, wherein the continuously enlarging section is shaped complementarily with the leading end of the pin.

4. The reference pin of claim 1, wherein the expandable front portion is nonpositively fastenable in a distal locking hole of an intramedullary nail using frictional forces.

5. The reference pin of claim 3, wherein the through hole has a discontinuously enlarging section adjoining the front end of the shaft.

6. The reference pin of claim 1, wherein the expandable front portion is integral with the shaft.

7. The reference pin of claim 2, wherein the pin enlarges towards the leading end.

8. The reference pin of claim 1, wherein the shaft comprises a shoulder at the transition between the rear portion and the expandable front portion, the shoulder being directed towards the front end of the shaft for abutting the outer surface of an intramedullary nail.

9. The reference pin of claim 1, further comprising:
a rotational securing arrangement permitting a defined positioning of the reference pin within a locking hole with regard to rotation about the longitudinal axis of the reference pin.

10. The reference pin of claim 1, wherein the shaft further comprises a depth indicator.

11. The reference pin of claim 10, wherein the depth indicator is arranged coaxially slideable at the lateral surface of the shaft.

12. The reference pin of claim 10, wherein the depth indicator is resiliently biased towards the front end of the shaft using a resilient member.

13. The reference pin of claim 1, wherein the spreading member comprises a nut member with an interior thread, and wherein the spreading member has an exterior thread terminally arranged towards its trailing end.

14. The reference pin of claim 1, further comprising:
a reference element with markers a position of which is one of acoustically and electromagnetically detectable using a position measurement device of a surgical navigation system.

15. The reference pin of claim 1, wherein the reference pin is made of a radiolucent material and wherein the reference pin further comprising:
at least two radiopaque markers.

16. The reference pin of claim 1, wherein the shaft comprises a threaded terminal rear portion and a stop axially spaced towards the front end of the shaft.

17. The reference pin of claim 1, wherein the shaft comprises at least one axial slot extending on at least the expandable front portion of the shaft.

18. An assembly for locking an intramedullary nail, comprising:
a reference pin including (a) a longitudinal shaft with a longitudinal axis, a front end, a rear end and a through hole penetrating the shaft from the front end to the rear end, the shaft including a rear portion adjoining the rear end and an expandable front portion adjoining the front end, the expandable front portion being insertable in a distal locking hole of an intramedullary nail and being reversibly expandable transversely to the longitudinal axis, the through hole having a continuously enlarging section adjoining the front end of the shaft, wherein the continuously enlarging section enlarges towards the front end; and (b) a spreading member moveably located in the through hole and being apt for reversibly expanding the expandable front end portion, wherein the expandable front portion is reversibly expandable within a range between 0.3 mm and 0.5 mm; and
a U-shaped drill guide having at least two guide holes which have bore axes extending transversely to the longitudinal axis of the reference pin, wherein the U-shape defines a plane which is not cut neither by one of the longitudinal axis of the reference pin and the bore axes.

19. An assembly for a fractured bone fixation, comprising:
a reference pin including (a) a longitudinal shaft with a longitudinal axis, a front end, a rear end and a through hole penetrating the shaft from the front end to the rear end, the shaft including a rear portion adjoining the rear end and an expandable front portion adjoining the front end, the expandable front portion being insertable in a distal locking hole of an intramedullary nail and being reversibly expandable transversely to the longitudinal axis, the through hole having a continuously enlarging section adjoining the front end of the shaft, wherein the continuously enlarging section enlarges towards the front end; and (b) a spreading member moveably located in the through hole and being apt for reversibly expanding the expandable front end portion, wherein the expandable front portion is reversibly expandable within a range between 0.3 mm and 0.5 mm; and
a U-shaped device fixating a fractured bone having a bow shaped member forming an arc in a plane which is not cut by the longitudinal axis of the reference pin, the device further including slots extending along an arc on the periphery of the bow shaped member, the device further including drill sleeves which are slideable in the slots and reversibly fastenable once located at a desired position.

* * * * *